(12) United States Patent
Huszár et al.

(10) Patent No.: US 6,211,382 B1
(45) Date of Patent: Apr. 3, 2001

(54) PROCESS FOR THE PREPARATION OF 1,3-DIAZA-SPIRO (4.4) NON-1-EN-4-ONE DERIVATIVES AND 1-CYANO-1-ACYLAMINOCYCLOPENTANE INTERMEDIATES

(75) Inventors: Csaba Huszár; Attila Kis-Tamás, both of Budapest; Attila Németh, Göd; Zsuzsanna Nád, Budapest; Zoltán Makovi, Budapest; Antal Gajáry, Budapest; Endre Kollár, Budapest; Péter Aranyosi, Budapest; Károly Gyüre, Dunakeszi; István Mészáros, Budapest; Zsuzsanna Csetriné Hári, Budapest; Attila Supic, Budapest; Ilona Dervalicsne Zrinyi, Budapest; Katalin Dubovszki, Budapest; Lajosné Páli, Budapest; Ágnes Kunsztné Kárász, Budapest; Erzsébet Bognár, Budapest, all of (HU)

(73) Assignee: Sanofi-Synthelabo, Paris (FR)

( * ) Notice: Subject to any disclaimer, the term of this patent is extended or adjusted under 35 U.S.C. 154(b) by 0 days.

(21) Appl. No.: 09/463,357

(22) PCT Filed: Jul. 22, 1998

(86) PCT No.: PCT/HU98/00068

§ 371 Date: Apr. 13, 2000

§ 102(e) Date: Apr. 13, 2000

(87) PCT Pub. No.: WO99/05120

PCT Pub. Date: Feb. 4, 1999

(30) Foreign Application Priority Data

Jul. 25, 1997 (HU) .................................................. 97 01295

(51) Int. Cl.[7] .................................................. C07D 235/02
(52) U.S. Cl. ...................................... 548/316.4; 558/432
(58) Field of Search ........................... 548/316.4; 558/432

(56) References Cited

U.S. PATENT DOCUMENTS

| 5,541,209 | 7/1996 | Spinale ................................. 514/381 |
| 5,559,233 | * 9/1996 | Bernhart et al. .............. 548/316.4 X |

(List continued on next page.)

FOREIGN PATENT DOCUMENTS

| 0532410 | 3/1993 | (EP) . |
| 0789019 | 8/1997 | (EP) . |

(List continued on next page.)

OTHER PUBLICATIONS

Granger R. & Techer H., Comptes Rendus Hebdomadaires Des Seances De L'Academie Des Sciences, vol. 250, No. 2, Apr. 4 1960, pp. 2581–2583.

(List continued on next page.)

*Primary Examiner*—Fiona T. Powers
(74) *Attorney, Agent, or Firm*—Birch, Stewart, Kolasch & Birch, LLP

(57) ABSTRACT

Process for the preparation of compounds of formula (I) wherein R means hydrogen atom, or $C_{1-6}$ alkyl group, or $C_{7-12}$ aralkyl group or phenyl group, characterised in that a) the compound of formula (III) is reacted with a compound of formula (IV) wherein X means halogen atom or $C_{1-5}$ alkoxy group or hydroxyl group, and the resulting compound of formula (II) is transformed, in a reaction medium with pH above 7, into the compound of formula (I) or b) the compound of formula (III) is reacted with an anhydride of general formula (V) and the resulting compound of formula (II) transformed, in a reaction medium with pH above 7, into the compound of formula (I), or c) a compound of formula (II) is transformed, in a reaction medium with pH above 7, into the compound of formula (I), and if desired, the resulting compounds of formula (I), before or after isolation, are transformed into acid addition salts, or the compounds of formula (I) are liberated from their acid addition salts. Thus a process for the preparation of intermediates useful in synthesis of angiotensin II antagonists is disclosed.

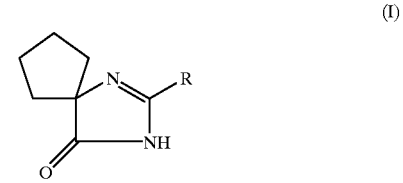

(I)

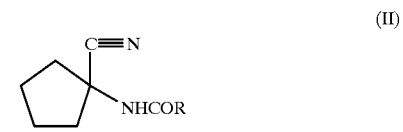

(II)

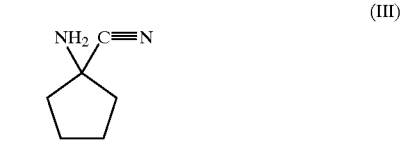

(III)

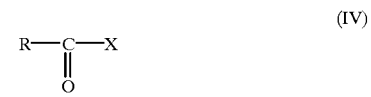

(IV)

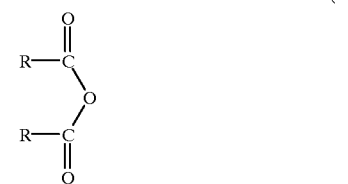

(V)

10 Claims, 1 Drawing Sheet

U.S. PATENT DOCUMENTS

| | | | | |
|---|---|---|---|---|
| 5,698,704 | * | 12/1997 | Jackson | 548/316.4 X |
| 5,910,595 | * | 6/1999 | Durrwachter | 548/316.4 X |
| 6,037,474 | * | 3/2000 | Drauz et al. | 548/316.4 |

FOREIGN PATENT DOCUMENTS

| | | |
|---|---|---|
| 9638406 | 12/1996 | (WO) . |
| 9736868 | 10/1997 | (WO) . |

OTHER PUBLICATIONS

Sudo R. & Ichihara S., Bulletin of the Chemical Society of Japan, vol. 36, No. 1, Jan. 1963, pp. 34–37.

Bernhart C.A. et al, Journal of Medicinal Chemistry, vol. 36, No. 22, 1993, pp. 3371–3380.

O'Brien P.M. et al, Journal of Medicinal Chemistry, vol. 37, No. 12, 1994, pp. 1810–1822.

* cited by examiner

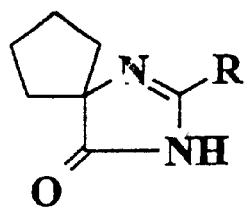  (I)
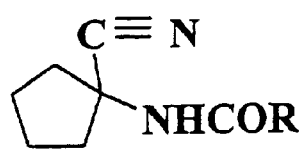  (II)
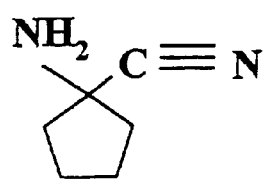  (III)
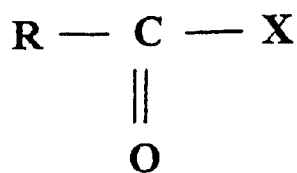  (IV)
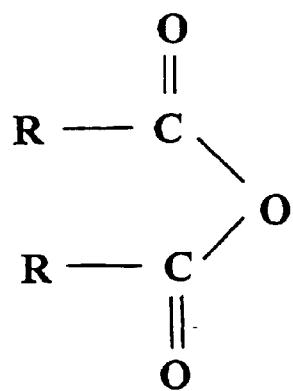  (V)

PROCESS FOR THE PREPARATION OF 1,3-DIAZA-SPIRO (4.4) NON-1-EN-4-ONE DERIVATIVES AND 1-CYANO-1-ACYLAMINOCYCLOPENTANE INTERMEDIATES

This application is the national phase under 35 U.S.C. § 371 of PCT International Application No. PCT/HU98/00068 which has an International filing date of Jul. 22, 1998, which designated the United States of America.

This invention relates to the new process for the preparation of compounds of general formula (I)—wherein R means hydrogen atom or $C_{2-6}$ alkyl group—and to the intermediates of general formula (II)—wherein the meaning of R is the same as above. Compounds of general formula (I) are important intermediates used in the course of preparation of active components of pharmaceuticals. They are e.g. applied in the synthesis of angiotensine II antagonists (PCT application, publication number WO-91/14679A).

Synthesis of 4-imidazolinones and their 2-substituted derivatives, constituting the main skeleton of compounds of general formula (I) is known from the literature (Bruckner: Szerves kémia Band III-1 page 296. Edition: Tankönyvkiadó, Budapest 1964). Takenaka and his co-workers described the preparation of 2-phenyl-4,4'-dialkyl-5-oxo-2-imidazolines in tetrahydrofuran-water heterogeneous system by a 5–12 hours reflux /Heterocycles 29 (6) p 1185 (1989)/. The above method is, however, difficult to implement since preparation of the appropriate carboxamides is problematic. The appropriate carboxamides are in general synthetised by partial hydrolysis of α-aminonitriles, thus, by that of the α-aminonmtrile (III). Taking into account the sensitivity of the aminonitriles against alkalines and oxidants, from the known methods only the partial hydrolysis performed in concentrated acidic medium is considered as feasible.

The transformation of nitrites into carboxamides in strongly acidic medium, preferably in concentrated sulfuric acid, raises, however, a number of problems. To be able to stir the reaction mixture, sufuric acid has to be applied in large excess. As a consequence, heating up the reaction mixture to 70° C. and cooling it down takes considerable time and keeping the reaction product for longer time in a concentrated sulfuric acidic medium will cause partial decomposition. This will cause the necessity of further purification steps. Since the aminocarboxamides are obtained in the form of sulfate salts, the amides have to be liberated. Neutralization of the large excess of acid means the addition of large amounts of base and also that of water, in order to keep the resulting salt in solution. The aminocarboxamide obtained is well solvated, its extraction from the reaction mixture requires a minimum 40-fold excess of the extracting solvent, even if the best—but from the aspect of health very unfavourable—chlorinated hydrocarbones are applied. These solvents, at that, can be recovered only with high losses. Our aim was to work out a novel process for the preparation of the compounds of general formula (I) eliminating the above problems.

We have found that if a) the compound of formula (III) is reacted with a compound of general formula (IV)—wherein R means hydrogen atom or $C_{2-6}$ alkyl group, X means halogen atom, $C_{1-5}$ alkoxy group or hydroxyl group—and the resulting compound of general formula (II)—wherein the meaning of R is the same as given above—is transformed, in a reaction medium with pH above 7, into the compound of general formula (I)—wherein the meaning of R is as defined above—, or b) the compound of formula (III) is reacted with an anhydride of general formula (V)—wherein the meaning of R is the same as defined above—, and the resulting compound of general formula (II)—wherein the meaning of R is as given above—is transformed, in a reaction medium with pH above 7, into the compound of general formula (I), or c) a compound of general formula (II)—wherein the meaning of R is the same as defined above—is transformed, in a reaction medium with pH above 7, into the compound of general formula (I), and, if desired, the resulting compounds of general formula (I), before or after isolation, are transformed into acid addition salts, or the compounds of general formula (I) are liberated from their acid addition salts, then the disadvantages of the known methods are avoided and the new method is also suitable for the "one-pot" synthesis of the compounds of general formula (I).

In the first, acylation step the use of acid chlorides is the most advantageous, in the presence of an organic solvent and an acid binding agent. As for organic solvents for example ethers (methyl tert-butyl ether), aromatic hydrocarbones e.g. toluene, xylene or chlorinated hydrocarbones e.g. dichloroethane can be applied, as for acid binding agents inorganic bases, for example alkali metal carbonates, alkali-earth metal oxides, organic bases e.g. trialkylamines may be employed. The resulting, if desired isolated, compounds of general formula (II) are new, they are not known from the literature.

Transformation of the compounds of general formula (II) was carried out in homogenous phase, in mixtures of water and organic solvent, preferably in aqueous alcohols, most preferably in aqueous methanol. The reaction is carried out in basic medium, above pH=7, for example in the presence of sodium hydroxide, but other alkali metal hydroxides, as well as alkali metal carbonates, alkali-earth metal hydroxides, alkali-earth metal carbonates or anion-exchange resins may also be used.

Cyclisation may be accomplished in 0,5–2 hours.

The cyclisation step is preferably carried out at a temperature between 50–160° C. The whole process can be carried out in one reaction pot and the resulting compounds of general formula (I) contain, at the highest 0,1% amount of contamination. The yield of the process is over 70%, calculated on the starting compound of formula (III). The compounds of general formula (I) are preferably isolated in the form of their organic or inorganic acid addition salts. Synthesis of the starting compound of formula (III) is known from the literature /it was synthesised according to the method of the PCT application, publ. number WO-91/14679 and of Org. Synt. 1955 3; (MS: (m/z) 110, 95, 81, 68, 54, 41, 28)/.

Further details of the invention are illustrated by the following examples.

EXAMPLE 1

1-cyano-1-n-pentanoylaminocyclopentane

To 11.0 g (0.1 mol) of 1-amino-1-cyanocyclopentane dissolved in 100 ml of dichloromethane, 15 ml 10. g (0.1 mol) of triethylamine was added, then dropwise 13 ml, 13 g (0.1 mol) of valeroyl chloride, while keeping the temperature at 25–35° C. The reaction mixture was stirred at 30–35° C. for 2 hours, then it was washed with water. The phases were separated, the organic phase was evaporated to obtain the pure title compound as an oil. The compound was identified by elementary analysis, IR, NMR and GC-MS spectrometry.

$^1$H-NMR (CDCl$_3$): δ0.81 (CH$_3$); 1.25 (CH$_2$); 1.51(CH$_2$); 2.14 (CH$_2$); 1.73 (m, ring, 1.2); 2.21 (ring 3H); 2.05 (ring 4H); 7.39 (1H, NH); $^{13}$C-NMR (CDCl$_3$): δ13.4(CH$_3$); 21.9 (CH$_2$); 27.3(CH$_2$); 35.4(CH$_2$); 22.7[2C(1,2)]; 38.4[2C (3.4)]; 54.6(C quaternary); 121.2(CN); 173.7(NH—CO); IR vmax: 2238(CN); 1654 (CO); 3304(NH); MS: (m/z) 194 (M+H), 165, 152, 137, 111, 102, 85, 51, 41, 29.

EXAMPLE 2

1-cyano- 1-n-pentanoylaminocyclopentane 11.0 g (0.1 mol) of 1-amino-1-cyanocyclopentane and 20.5 g (0.11 mol) of valeric anhydride were refluxed for 3 hours. The reaction mixture was evaporated under vacuo to constant weight. The resulting 19,3 g oil (98.5%) was identical with the product obtained in Example 1.

EXAMPLE 3

1-cyano-1-n-pentanoylaminocyclopentane 11.0 g (0.1 mol) of 1-amino-1-cyanocyclopentane and 20.4 g (0.2 mol) of valeric acid were placed in an apparatus equipped with water-separatory distillation head and boiled until 1.8 ml of water distilled off. The reaction mixture was then evaporated in fine vacuum to constant weight. 19.1 g (97.4%) of oily product was obtained, which was identical with the product obtained in Example 1.

EXAMPLE 4

1-cyano-1-n-pentanoylaminocyclopentane 11.0 g (0. mol) of 1-amino-1-cyanocyclopentane, 13.9 g (0.12 mol) of methyl valerate and 1.0 g sodium methylate were boiled for 16 hours. The volatile products were then distilled off in vacuo. To the residue 50 ml of water was added, the pH was adjusted to neutral by the addition of acetic acid and the mixture was extracted with 70 ml followed by 2×50 ml of dichloroethane. The combined organic phases were dried over sodium sulfate and evaporated in vacuo to constant weight. 13.1 g (66.8%) of oily product was obtained which was identical with the product obtained in Example 1.

EXAMPLE 5

1-cyano-1-formylaminocyclopentane 11.0 g (0.1 mol) of 1-amino-1-cyanocyclopentane and 10 ml of 85% formic acid were placed in an apparatus equipped with water-separatory distillation head and boiled for 3 hours. The reaction mixture was then evaporated to constant weight in vacuo.

12.4 g (90%) of oily product was obtained which on investigation by GC-MS gave the following fragments of the title product M: 138, 137, 123, 111, 110, 109, 93, 81, 68, 66, 46, 41 (R$_t$: 10.7')

EXAMPLE 6

2-butyl-1,3-diaza-spiro[4.4]non-1-en4-one monohydrochloride

To 19.6 g (0.1 mol) of 1-cyano-1-n-pentanoylaminocyclopentane dissolved in 70 ml of methanol, 25 g (0,46 mol) of potassium hydroxide dissolved in 50 ml of water was added. The resulting solution was stirred and heated at 50–60° C., then under reflux conditions for 2,5 hours. The pH was decreased by the addition of 25 g of ammonium chlorid, then methanol was distilled off. The residue was extracted with 50 ml and 2×30 ml of toluene, the combined organic phases were evaporated to constant weight The residual 16 g of title compound was dissolved in 100 ml of acetone, the pH of the resulting solution was adjusted to 1–2 with hydrochloric acid solution, the mixture was crystallized, the crystals were collected by filtration to obtain 14 g of the title compound, yield 60.8%.

IR: 3600–2200 : vibr, NH; 1779: γc=o; 1642 γc, 1517: δNH (IRFT Perkin Elmer)

1H NMR: 0.9 ppm T (CH$_3$); 1.34 ppm S (CH$_2$); 1.73 ppm Q (CH$_2$); 1.78–2.01 ppm M cyclopentane (CH$_2$); 2.78 ppm T (CH$_2$); 9–15 ppm (NH, N)

MS: 194, 179, 166, 165, 152, 124, 84, 83, 54, 41

TLC: eluant: chloroform:methanol 6:1, TLC plate: Kieselgel GF254

Detection by: I$_2$ vapors; Rf=0,64

EXAMPLE 7

2-butyl-1,3-diaza-spiro[4.4]non-1-en-4one

To 19.6 g (0,1 mol) of 1-cyano-1-n-pentanoylaminocyclopentane dissolved in 70 ml of methanol, 5 g of Varion AD resin was added the reaction mixture was heated under reflux conditions for 3 hours. After filtration and evaporation 16.5 g (71.7%) of title compound was obtained, assay by GC: 92%.

What is claimed is:

1. A process for the preparation of a compound of formula (I), wherein R means hydrogen atom, or C$_{1-6}$ alkyl group, or C$_{7-12}$ aralkyl group or phenyl group, characterized in that a) the compound of formula (III) is reacted with a compound of formula (IV), wherein the meaning of R is the same as defined above, and X means halogen atom or C$_{1-5}$ alkoxy group or hydroxyl group, and the resulting compound of formula (II), wherein the meaning of R is the same as given above, is transformed, in a reaction medium with pH above 7, into the compound of formula (I), wherein the meaning of R is as defined above; or b) the compound of formula (III) is reacted with an anhydride of formula (V), wherein the meaning of R is the same as defined above, and the resulting compound of formula (II), wherein the meaning of R is as given above, is transformed, in a reaction medium with pH above 7, into the compound of general formula (I); or c) a compound of formula (II), wherein the meaning of R is the same as defined above, is transformed, in a reaction medium with pH above 7, into the compound of formula (I), and optionally, the resulting compound of formula (I), before or after isolation, is transformed into an acid addition salt, or the compound of formula (I) is liberated from its acid addition salt

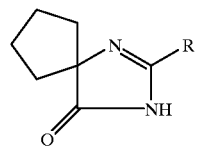

(I)

-continued

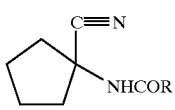
(II)

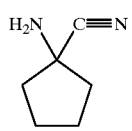
(III)

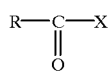
(IV)

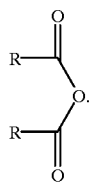
(V)

2. The process according to claim 1, wherein the reaction is carried out in a homogeneous phase.

3. The process according to claim 1, wherein the reaction is carried out in a heterogeneous phase.

4. The process according to claim 1, wherein a base is utilized in the reaction, and said base is selected from the group consisting of alkali alcoholates, alkali metal hydroxides, alkali metal carbonates and ion exchange resins.

5. The process according to claim 1, wherein the reaction taking place between the compound of formula (III) and the compound of formula (IV) or (V) utilizes an acid binding agent.

6. The process according to claim 5, wherein the acid binding agent is selected from the group consisting of amines, alkali-earth metal carbonates, alkali-earth metal carbonates and alkali-earth metal oxides.

7. The process according to claim 1, wherein a solvent is utilized in the reaction, and said solvent is an aromatic hydrocarbon, a halogenated aliphatic hydrocarbon, an aliphatic ether, an alcohol, a homogenous or a heterogeneous aqueous solvent system formed between the above solvents and water.

8. The process according to claim 3, wherein a phase transfer catalyst and/or a dissolution transfer is used.

9. The process according to claim 7, wherein the phase transfer catalyst is selected from the group consisting of alkyl ammonium hydrogen sulfates, hydrogen halogenides and hydroxides, and for the dissolution transfer longer chain alcohols are used.

10. The process according to claim 1, wherein the reaction is carried out without isolating the compound of formula (II).

* * * * *